US012673979B2

(12) United States Patent
Tafalla Piñeiro et al.

(10) Patent No.: US 12,673,979 B2
(45) Date of Patent: Jul. 7, 2026

(54) PLASMID ENCODING B-CELL ACTIVATING FACTOR RECEPTOR (BAFF-R) AND USES OF SAME IN THE TREATMENT AND PREVENTION OF INFLAMMATORY DISEASES IN FISH

(71) Applicants:CONSEJO SUPERIOR DE INVESTIGACIONES CIENTIFICAS (CSIC), Madrid (ES); THE UNIVERSITY COURT OF THE UNIVERSITY OF ABERDEEN, Aberdeen (GB)

(72) Inventors: Carolina Tafalla Piñeiro, Madrid (ES); Estefanía Muñoz Atienza, Madrid (ES); Christopher J. Secombes, Aberdeen (GB); Jason W. Holland, Aberdeen (GB); Marc Faber, Aberdeen (GB)

(73) Assignees: CONSEJO SUPERIOR DE INVESTIGACIONES CIENTIFICAS (CSIC), Madrid (ES); THE UNIVERSITY COURT OF THE UNIVERSITY OF ABERDEEN, Aberdeen (GB)

( * ) Notice: Subject to any disclaimer, the term of this patent is extended or adjusted under 35 U.S.C. 154(b) by 1043 days.

(21) Appl. No.: 17/778,232

(22) PCT Filed: Nov. 19, 2020

(86) PCT No.: PCT/ES2020/070721
§ 371 (c)(1),
(2) Date: Nov. 21, 2022

(87) PCT Pub. No.: WO2021/099667
PCT Pub. Date: May 27, 2021

(65) Prior Publication Data
US 2023/0159604 A1 May 25, 2023

(30) Foreign Application Priority Data
Nov. 19, 2019 (ES) ............................... ES201931006

(51) Int. Cl.
$A61K\ 38/04$ (2006.01)
$A61P\ 13/12$ (2006.01)
(Continued)

(52) U.S. Cl.
CPC .............. *C07K 14/55* (2013.01); *A61P 13/12* (2018.01); *A61P 33/00* (2018.01); *C07K 14/461* (2013.01);
(Continued)

(58) Field of Classification Search
None
See application file for complete search history.

(56) References Cited

U.S. PATENT DOCUMENTS 8,617,545 B2 * 12/2013 Hsu ...................... C12Q 1/6883
514/19.3
9,290,582 B2 * 3/2016 Yang ...................... A61P 43/00

FOREIGN PATENT DOCUMENTS

CA      2534927 A1    8/2006
CN    107469076 A * 12/2017 ............. A61K 39/12
(Continued)

OTHER PUBLICATIONS

Strohl, W.R., Fusion Proteins for Half-Life Extension of Biologics as a Strategy to Make Biobetters, BioDrugs, 29:215-239, 2015.*
(Continued)

*Primary Examiner* — Claire Kaufman
(74) *Attorney, Agent, or Firm* — Hayes Soloway PC

(57) ABSTRACT
The present invention relates to a plasmid that encodes a fusion protein comprising a signal peptide and the extracellular domain of the B-cell activating factor receptor (BAFF-
(Continued)

R), and optionally, a fragment of the constant region (Fc) of an immunoglobulin. The invention also relates to compositions comprising said plasmid, and to the use of same in the treatment and/or prevention of inflammatory diseases in fish, more preferably in salmonids.

16 Claims, 3 Drawing Sheets

Specification includes a Sequence Listing.

(51) Int. Cl.

| | |
|---|---|
| *A61P 33/00* | (2006.01) |
| *C07K 14/46* | (2006.01) |
| *C07K 14/55* | (2006.01) |
| *C07K 14/705* | (2006.01) |
| *C07K 19/00* | (2006.01) |
| *C12N 15/62* | (2006.01) |
| *C12N 15/85* | (2006.01) |

(52) U.S. Cl.
CPC ...... *C07K 14/70578* (2013.01); *C12N 15/625* (2013.01); *C12N 15/85* (2013.01); *C07K 2319/02* (2013.01); *C07K 2319/035* (2013.01); *C12N 2800/106* (2013.01)

(56) References Cited

FOREIGN PATENT DOCUMENTS

| | | | | |
|---|---|---|---|---|
| EP | 2325317 A1 * | 5/2011 | .............. | A61P 37/00 |
| ES | 2321789 A1 | 6/2009 | | |
| WO | 2006035084 A1 | 4/2006 | | |
| WO | 2008077413 A1 | 7/2008 | | |
| WO | 2014041189 A1 | 3/2014 | | |
| WO | 2014191759 A1 | 12/2014 | | |

OTHER PUBLICATIONS

NovoPro, Commonly used leader peptide sequence for mammalian cell expression, Retrieved online from <URL:https://www. novoprolabs.com/support/articles/commonly-used-leader-peptide-sequences-for-efficient-secretion-of-a-recombinant-protein-expressed-inmammalian-cells-201804211337.html> [retrieved on Jul. 23, 2025], 2018.*

Pandit et al., Identification of TNF13b (BAFF) gene from grass carp (*Ctenopharyngodon idella*) and its immune response to bacteria and virus, Dev. Compar. Immunol. 39:460-464, 2013.*

US Fish & Wildlife Services, https://www.fws.gov/sites/default/files/documents/Fish%20Health%20News%20You%20Can%20Use%20April%202020%20Edition%20.pdf, 13 pages, Apr. 2020.*

Mashoof et al., Fish immunoglobulins, Biology 2016, 5(4), 45; https://doi.org/10.3390/biology5040045, 23 pages, 2013.*

NCBI GenBank Database, Accession No. AQZ26593, TNFR13C [Retrieved online from: Oncorhynchus mykiss], Retrieved online from: <URL:https://www.ncbi.nlm.nih.gov/protein/AQZ26593> [retrieved on Jan. 20, 2026], Mar. 29, 2017.*

UniProt Database, Accession No. Q96RJ3, TR13C_Human, Retrieved online from: <URL:https://www.uniprot.org/uniprotkb/Q96RJ3/entry#structure> [retrieved on Jan. 20, 2026], 2026.*

Zhang et al., Conservation of structural and functional features in a primordial CD80/86 molecule from rainbow trout (*Oncorhynchus mykiss*), a primitive teleost fish, J. Immunol. 183(1):83-96, 2009.*

Aitor G. Granja, et al. "Characterization of BAFF and APRIL subfamily receptors in rainbow trout (*Oncorhynchus mykiss*). Potential role of the BAFF/APRIL axis in the pathogenesis of proliferative kidney disease", Article, 2017, 1-24, Plos One.

Jana Montero, et al. "Specific Regulation of the Chemokine Response to Viral Hemorrhagic Septicemia Virus at the Entry Site", Journal, 2011, 4046-4056, vol. 85, No. 9, Journal of Virology.

Beth Okamura, et al. "Life Cycle Complexity, Environmental Change and the Emerging Status of Salmonid Proliferative Kidney Disease", Article, 2011, 735-753, No. 56, Freshwater Biology.

Kenneth J. Livak et al., "Analysis of Relative Gene Expression Data Using Real-Time Quantitative PCR and the 2-ΔΔCT Method", Journal, 2001, 402-408, No. 25, Methods.

D.S. Grabner et al., "Tetracapsuloides bryosalmonae (Myxozoa: Malacosporea) portal of entry into the fish host", Article, 2010, 197-206, vol. 90, Diseases of Aquatic Organisms.

* cited by examiner

1

PLASMID ENCODING B-CELL ACTIVATING FACTOR RECEPTOR (BAFF-R) AND USES OF SAME IN THE TREATMENT AND PREVENTION OF INFLAMMATORY DISEASES IN FISH

CROSS-REFERENCE TO RELATED APPLICATIONS AND PRIORITY

This patent application claims priority from PCT Application No. PCT/ES2020/070721 filed Nov. 19, 2020, which claims priority from Spanish Patent Application No. P201931006 filed Nov. 19, 2019. Each of these patent applications are herein incorporated by reference in their entirety.

DESCRIPTION

The present invention is included in the technical sector of aquaculture, specifically in the treatment and prevention of diseases that cause B-cell mediated inflammation. Thus, the invention relates to a plasmid comprising a nucleotide sequence that encodes a fusion protein comprising a signal peptide and the extracellular domain of the B-cell activating factor receptor (BAFF-R), and optionally, an Fc fragment of an immunoglobulin. In particular, the present invention also discloses the use of said plasmid and of compositions comprising it as a medicament, and more specifically, for the treatment and/or prevention of diseases that cause B-cell mediated inflammation in fish, more preferably in salmonids.

REFERENCE MATERIALS

Various sequence listings and variant listings are provided herein and attached in a separate sequence listing .txt file. The sequence listing is provided in a .txt file entitled 'Pons_2226_English_Sequence.txt' created on 2022 Nov. 21 and is 19,559 bytes in size. This sequence listing is incorporated herein by reference.

BACKGROUND OF THE INVENTION

The growth of intensive aquaculture has caused an increase in the incidence of inflammatory diseases in fish caused by viruses, bacteria or parasites. In this sense, the incidence of diseases that cause B-cell mediated inflammation, such as Proliferative Kidney Disease (PKD) caused by the myxozoan *Tetracapsuloides bryosalmonae*, or the Red Mark Syndrome, is increasingly common in salmonid aquaculture in both Europe and North America (Grabner, D. S., and M. El-Matbouli. Dis. Aquat. Organ. 2010; 90: 197-206; Okamura, B., et al. Freshwater Biol. 2011; 56: 735-753). In Spain, PKD disease has been identified as one of the biggest problems in Rainbow trout (*Oncorhynchus mykiss*) farming, causing significant economic losses in this sector, mainly during the summer months when the water reaches a temperature higher than 15° C., which favours parasite proliferation and infection.

The myxozoan *T. bryosalmonae* has a double host cycle which affects different salmonid species and the bryozoan *Fredericella sultana*, which is the invertebrate host. Bryozoans infected by this parasite release malacospores into the water that invade the gills of salmonids. Subsequently, the parasite migrates through the vascular system to the kidney and spleen, these organs being the main target organs for their development and proliferation in salmonids. When the water temperature is higher than 15° C., the extrasporogonic proliferation and development of *T. bryosalmonae* in the interstitial tissue of the kidney in salmonids produces chronic inflammation characterized by lymphocytic hyperplasia, the formation of granulomatous lesions, renal atrophy and hypersecretion of immunoglobulins by the B lymphocytes. As a result of immune system deregulation after parasitic infection, fish are more susceptible to secondary infections and mortalities can reach up to 100%. In contrast, when the water temperature is lower than 15° C., the host develops a moderate immune response against the parasite, associated with fewer clinical symptoms and low mortality.

Eukaryotic expression plasmids that encode a vaccine antigen have been used in fish as vaccines. In this sense, international patent application WO2006035084 describes gene constructs comprising the coding sequence for immunogenic peptides of pathogens of aquatic animals and the use of said constructs as vaccines for the prevention of infectious diseases in aquatic animals. Furthermore, international patent application WO2008077413A1 describes the use, method and formulation of inclusion of DNA vaccines in food compositions for livestock animals, in particular in aquacultural systems. Patent ES2321789B1 also describes the use of an expression vector as an immunostimulant or adjuvant for DNA vaccines and to prevent infection of fish by a rhabdovirus, such as Viral Hemorrhagic Septicemia Virus (VHSV) and infectious Hematopoietic Necrosis Virus (IHNV). Furthermore, international patent application WO2014041189A1 also describes nucleic acids, as well as vaccines comprising said nucleic acids, and the use of same against the agents that cause Salmon Pancreas Disease (SPD) caused by a salmonid alphavirus (SAV).

It is important to mention that, until 2017, the injection of expression vectors or plasmids for the prevention of diseases in aquaculture was not allowed in fish intended for human consumption in the European Union, but it was precisely in that year when the European Commission approved the use of a DNA vaccine for intramuscular injection in aquaculture. Specifically, it involves the injection of the pUK-SPDV-poly2 #1 plasmid, marketed as Clynav, Elanco GmbH, Germany, to protect Atlantic salmon (*Salmo salar*) against SPD caused by salmonid alphavirus subtype 3 (SAV3) (CVMP assessment report for CLYNAV (EMEA/V/C/002390/0000). *Salmon pancreatic disease vaccine (recombinant DNA plasmid)*).

On the contrary, there are no commercial treatments to prevent and/or treat PKD or the red mark syndrome in salmonids, since the use of effective compounds against the parasite *T. bryosalmonae*, such as malachite green and fumagillin, are not registered in the European Union for use in aquaculture due to their harmful effects on the health of humans who consume said animals. To that end, taking into account that the incidence of this disease is increasing, in the state of the art there is a need to develop useful compounds for the treatment of pathologies that cause B-cell mediated inflammation, such as, for example, the PKD disease caused by the myxozoan *T. bryosalmonae* or the red mark syndrome, in salmonids. Said compounds and/or prevention and/or treatment systems should be, advantageously, easy and cost-effective in terms of production and administration.

DESCRIPTION OF THE INVENTION

To solve the aforementioned technical problem, the inventors have used the strategy of inhibiting the signaling mediated by the cytokine BAFF (B-cell activating factor), which is involved in processes of maturation, activation of B lymphocytes, and development and activation of lymphoid organs. This cytokine performs important regulatory functions by inducing pleiotropic responses through its interaction with three receptors: TACI, BCMA and BAFF-R, whose expression is fundamentally restricted to B and T lymphocytes. To carry out this strategy, eukaryotic expression plasmids have been designed which comprise sequences that encode for each of the soluble regions of each BAFF receptor, specifically BAFF-R, TACI and BCMA, independently. Thus, the administration of said plasmids, by intramuscular route, is capable of inhibiting the inflammatory response, and therefore, they are useful in the treatment of infections that cause B-cell mediated inflammation, such as, for example, PKD and the red mark syndrome, in salmonids, preferably in Rainbow trout.

In particular, the present invention relates to the synthesis of a fusion protein comprising an amino acid sequence comprising the soluble region (extracellular domain) of BAFF-R, or the soluble region of TACI, or the soluble region of BCMA, from Rainbow trout, bonded immediately after an amino acid sequence comprising the Rainbow trout interleukin-2 (IL-2) signal peptide; and when said fusion protein is administered to the Rainbow trout, preferably comprised in a plasmid, it is able to block the activity of the cytokine BAFF, thus being useful in the treatment of infections that cause B-cell mediated inflammation, such as, for example, PKD and the red mark syndrome. In particular, PKD is associated with a large increase in the expression levels of the cytokine BAFF and is caused by infection with the parasite *T. bryosalmonae*. Thus, through said fusion proteins, included independently in a plasmid that is administered to infected animals, the pathology associated with said infection is reduced, and therefore, mortality it entails is reduced, especially in summer when the water temperature is higher than 15° C.

As mentioned earlier, the treatment of infections in aquaculture has been mainly based on the use of vaccines comprising antigens of the pathogen; in contrast, the present invention is aimed at obtaining molecules, specifically plasmids or vectors, comprising nucleotide sequences that encode endogenous peptide-based fusion proteins of the host, with the purpose of blocking immunological pathways that are altered when the animal has been infected by a pathogen, therefore being useful in the treatment and/or prevention of said infections.

As shown in the examples included herein, the administration of the plasmid comprising the nucleotide sequence that encodes the aforementioned fusion protein in trout naturally infected with the parasite *T. bryosalmonae* reduces the degree of kidney inflammation and the mortality of said animals (Example 4), as well as the parasitic load in animals treated with the plasmid of the invention (Example 5).

Thus, in a first aspect, the present invention relates to a fusion protein, hereinafter called fusion protein of the invention, comprising a first amino acid sequence having at least 95%, 96%, 97%, 98%, 99% identity to an amino acid sequence as shown in SEQ ID NO: 2, fused to a second amino acid sequence, wherein said second amino acid sequence has at least 95%, 96%, 97%, 98%, 99% identity to an amino acid sequence as shown in SEQ ID NO: 4.

The first amino acid sequence that forms the fusion protein of the invention corresponds to a sequence that encodes a signal peptide; preferably it is an amino acid sequence that encodes the interleukin-2 (IL-2) signal peptide. For purposes of the present invention, the IL-2 signal peptide comes from Rainbow trout and corresponds to amino acids 1 to 20 of the protein with accession number CAM12545.1 in the NCBI (National Center for Biotechnology Information) database.

For purposes of the present invention, the term "signal peptide", "signal sequence" or "localization signal peptide", used interchangeably herein, refers to a short peptide (5-30 amino acids in length) present at the N-terminus which directs protein transport into the secretory pathway. The signal peptide directs translocation into the endoplasmic reticulum of the protein to which it is bonded. During or after translocation, the signal peptide is cleaved by a signal peptidase, generating a free signal peptide and a secreted mature protein. Signal peptides suitable for use in the present invention include, but are not limited to, signal peptides, capable of directing a protein to the cell membrane, to the nucleus, to the nuclear membrane, to the mitochondrial matrix, to the mitochondrial membrane, to the endoplasmic or sarcoplasmic reticulum, to the cytoplasm, to the Golgi complex, to the chloroplast, to the apoplast or to the peroxisome. In a preferred embodiment, the signal peptide of the fusion protein of the invention is the Rainbow trout IL-2 signal peptide (SEQ ID NO: 2).

The second amino acid sequence of the fusion protein of the invention corresponds to the extracellular domain of the BAFF receptor (BAFF-R) from Rainbow trout (SEQ ID NO: 4). The extracellular domain of BAFF-R corresponds to amino acids 21 to 75 of the protein with accession number AQZ26593 in the NCBI database. BAFF-R is a membrane receptor belonging to the tumour necrosis factor (TNF) receptor and ligand superfamily and it is responsible for regulating B-cell survival, proliferation and differentiation.

In a preferred embodiment, the fusion protein of the invention comprises a first amino acid sequence such as SEQ ID NO: 2 and a second amino acid sequence such as SEQ ID NO: 4. In another more preferred embodiment, the fusion protein of the invention comprises SEQ ID NO: 8.

In another preferred embodiment, the fusion protein of the invention further comprises an amino acid sequence of an Fc domain of an immunoglobulin (Ig). In a more preferred embodiment, the Fc domain belongs to a mouse immunoglobulin G (IgG), selected from IgG1, IgG2, IgG3 and IgG4 isotypes, as well as any allotype within each group of isotypes. The Fc domain of an IgG in the fusion protein of the invention allows for the detection and purification of said fusion protein. In a more preferred embodiment, the Fc domain of a mouse IgG1 comprises an amino acid sequence having at least 95, 96, 97, 98 and 99% identity to SEQ ID NO: 6. In another even more preferred embodiment, the Fc domain of the mouse IgG1 is SEQ ID NO: 6.

In another preferred embodiment, the fusion protein of the invention comprises an amino acid sequence with at least 95, 96, 97, 98, 99% identity to SEQ ID NO: 10. More preferably, the fusion protein of the invention comprises SEQ ID NO: 10.

The combination of polypeptides to provide a fusion protein can be achieved by several means, for example: chemically by direct coupling or through an intermediate structure; or by molecular biological fusion, through the combination of recombinant nucleic acid molecules comprising nucleic acid fragments capable of encoding the two, such that a single continuous expression product is finally produced. Thus, for purposes of the present invention, the term "fused to" or "bonded to", used interchangeably herein, refers to, but is not limited to, a polypeptide or fusion protein formed by the expression of a chimeric nucleotide sequence created by combining more than one sequence, generally by cloning a gene in an expression vector in a frame with a second gene such that the two genes encode a continuous polypeptide.

The term "identity", "percent identity" or "sequence identity" between two sequences (nucleic acids or proteins) is understood as designating a percentage of identical nucleotides or amino acids between the two sequences that are compared, which is obtained after the best alignment, said percentage being purely statistical and the differences between the two sequences being distributed randomly and along the entire length thereof. "Best alignment" or "optimal alignment" is understood as designating the alignment by which the percent identity determined, as described below, is the highest. Comparisons between two nucleotide or amino acid sequences are typically carried out by comparing these sequences after they have been optimally aligned, said comparison being carried out by segment or by "comparison window" to identify and compare the local regions of sequence similarity. Optimal alignment of these sequences for their comparison can be performed, in particular, with the help of one of the following algorithms: Smith and Waterman's local homology algorithm (1981), Neddleman and Wunsch's local homology algorithm (1970), Pearson and Lipman's search for similarity method (1988), computer programs that use these algorithms (GAP, BESTFIT, BLASTP, BLASTN, BLASTX, TBLASTX, FASTA and TFASTA in the Wisconsin Genetics Software package (Genetics Computer Group, 575 Science Dr., Madison, WI), or internet servers, in particular those of the National Center for Biotechnology Information (NCBI) (www.ncbi.nlm.nih-.gov), EMBL (www.embl.org) and the Ensembl project (www.ensembl.org). To obtain the optimal alignment, the BLAST program is preferably used, with the BLOSUM 62 matrix. PAM or PAM250 matrices can also be used, as well as an identity matrix for the nucleotide sequences.

In a second aspect, the present invention relates to a nucleic acid, hereinafter called nucleic acid of the invention, which encodes the fusion protein according to the invention. In a preferred embodiment, the nucleic acid of the invention comprises a first nucleotide sequence comprising at least 95, 96, 97, 98, 99% identity to SEQ ID NO: 1, more preferably SEQ ID NO: 1, fused to a second nucleotide sequence comprising at least 95, 96, 97, 98, 99% identity to SEQ ID NO: 3, more preferably SEQ ID NO: 3. In another more preferred embodiment, the nucleic acid of the invention comprises a nucleotide sequence that has at least 95, 96, 97, 98, 99% identity to SEQ ID NO: 7, more preferably the nucleic acid of the invention comprises SEQ ID NO: 7.

In another more preferred embodiment, the nucleic acid of the invention further comprises a nucleotide sequence that encodes the Fc domain of mouse IgG1, wherein said nucleotide sequence comprises at least 95, 96, 97, 98, 99% identity to SEQ ID NO: 5, more preferably SEQ ID NO: 5.

In another more preferred embodiment, the nucleic acid of the invention comprises a nucleotide sequence comprising at least 95, 96, 97, 98, 99% identity to SEQ ID NO: 9, more preferably comprising SEQ ID NO: 9.

In another aspect of the invention, this relates to an expression vector or plasmid, hereinafter vector or plasmid of the invention, which comprises the nucleic acid of the invention, wherein, optionally, said nucleic acid is operably bonded to an expression control sequence suitable for expression in a host cell.

The term "expression vector" or "expression plasmid", used interchangeably herein, refers to a DNA fragment that has the ability to replicate in a given host and can serve as a carrier to carry out the transcription of a sequence of interest that has been inserted into the same. The expression vector or plasmid can also be incorporated into a cosmid, a bacteriophage, a viral vector, without excluding vectors of another type corresponding to the provided definition of vector.

For purposes of the present invention, the term "operably bonded", as used herein, refers to a control sequence, for example, a promoter or operator, which is suitably placed in a position relative to a coding sequence such that the control sequence directs the production of a polypeptide encoded by the coding sequence.

An expression vector or plasmid in the context of the present invention may be any suitable vector or plasmid, including chromosomal, non-chromosomal and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA and viral nucleic acid vectors (RNA or DNA).

Useful expression vectors or plasmids for eukaryotic hosts include, for example, vectors or plasmids comprising expression control sequences of SV40, bovine papilloma virus, adenovirus, adeno-associated viruses, cytomegalovirus and retrovirus.

The expression control sequences are designed to control and direct the transcription of genes of interest and the subsequent expression of proteins in various cell systems or sites of interest. The plasmids combine an expressible nucleotide sequence or gene of interest with expression control sequences (i.e., expression cassettes) comprising desirable elements such as, for example, promoters, enhancers, selectable markers, operators, etc. In the expression vector or plasmid of the invention, the nucleic acid molecules that encode the fusion protein of the invention may comprise or be associated with any promoter, enhancer, selectable marker, operator, repressor protein, polyA termination sequences and other expression-facilitating elements.

For purposes of the present invention, the term "promoter" refers to a DNA sequence sufficient to direct the transcription of a DNA sequence to which it is operably bonded, as described previously. Examples of useful expression promoters in the present invention are constitutive promoters such as, for example, the human cytomegalovirus (CMV) promoter/enhancer or CMV major IE (CMV-MIE) promoter, as well as the Rous sarcoma virus (RSV) promoter, simian virus 40 (SV40) late promoter, SL3-3 promoters, MMTV, ubiquitin (Ubi), ubiquitin C (UbC) and HIV LTR.

In a preferred embodiment, the vector or plasmid of the invention comprises a promoter selected from the group consisting of SV40, CMV, RSV, SL3-3, MMTV, Ubi, UbC and HIV LTR. In another even more preferred embodiment, the promoter is CMV.

The nucleic acid molecules of the invention may also be operably bonded to an effective poly(A) termination sequence, an origin of replication for the plasmid product in E. coli, an antibiotic resistance gene as a selectable marker and/or a convenient cloning site (e.g., a polylinker). The nucleic acids may also comprise a regulatable inducible promoter (inducible, repressible, developmentally regulated) as opposed to a constitutive promoter such as the CMV IE (a person skilled in the art will recognize that said terms are actually descriptors of a degree of gene expression under certain conditions).

The selectable markers are well-known elements in the art. Under the selective conditions, only cells that express the appropriate selectable marker can survive. Commonly, selectable marker genes express proteins, usually enzymes, which confer resistance to various antibiotics in cell cultures. Under other selective conditions, cells that express a fluorescent protein marker are made visible and, therefore, are selectable. The embodiments include beta-lactamase (bla) (beta-lactam antibiotic resistance gene or ampicillin resistance gene or ampR), bls (blasticidin resistance acetyl transferase gene), bsd (blasticidin-S-deaminase resistance gene), bsr (blasticidin-S resistance gene), Sh ble (Zeocin® resistance gene), hygromycin phosphotransferase (hpt) (hygromycin resistance gene), tetM (tetracycline resistance gene or tetR), neomycin phosphotransferase II (npt) (neomycin resistance gene or neoR), kanR (kanamycin resistance gene) and pac (puromycin resistance gene).

In certain embodiments, the vector or plasmid of the invention comprises one or more selectable marker genes selected from the group consisting of bla, bls, BSD, bsr, Sh ble, hpt, tetR, tetM, npt, kanR and pac. In other embodiments, the vector comprises one or more selectable marker genes that encode green fluorescent protein (GFP), enhanced green fluorescent protein (eGFP), cyan fluorescent protein (CFP), enhanced cyan fluorescent protein (eCFP) or yellow fluorescent protein (YFP).

In another more particular embodiment, the plasmid of the invention comprises SEQ ID NO: 11.

In another aspect, the present invention relates to a host cell comprising the nucleic acid molecule or the vector of the invention.

For purposes of the present invention, the term "host cell" includes any type of cell that is susceptible to transformation, transfection, transduction and the like with a nucleic acid construct or expression vector comprising a nucleotide or polynucleotide sequence that encodes the fusion protein of the invention. The choice of a host cell will largely depend on the nucleotide sequence encoding the polypeptide and its source. The host cell may be eukaryotic, such as a mammalian, insect, bird, fish, amphibian, reptilian, plant or fungal cell. The choice of a suitable host cell may also be influenced by the choice of the detection signal. For example, the use of constructs with reporter genes (e.g., lacZ, luciferase, thymidine kinase or green fluorescent protein "GFP") can provide a selectable signal by activating or inhibiting transcription of the gene of interest in response to a transcriptional regulatory protein. In order to achieve optimal selection or "screening", the phenotype of the host cell must be considered.

A host cell of the present invention includes prokaryotic and eukaryotic cells. Prokaryotes include Gram-negative organisms (e.g., *Escherichia coli*) or Gram-positive organisms (e.g., bacteria of the genus *Bacillus*). Prokaryotic cells will be used, preferably, for the propagation of the transcriptional control sequence of the vector containing the polynucleotide(s) object(s) of the invention, which will make it possible to achieve a greater number of copies of the vector containing the polynucleotide(s) object(s) of the invention. Prokaryotic host cells suitable for the transformation of this vector include, for example, but are not limited to, *E. coli, Bacillus subtilis, Salmonella typhimurium*, and other species within the genera *Enterococcus, Lactococcus, Pseudomonas, Streptomyces* and *Staphylococcus*. In a more particular embodiment, the prokaryotic host cell of the invention is an *E. coli* cell. Eukaryotic cells include, inter alia, yeasts, insect cells, mammalian cells, and cells of parasitic organisms (e.g., Trypanosomes). Culture systems with mammalian host cells include established cell lines such as COS cells, L cells, 3T3 cells, Chinese hamster ovary (CHO) cells, embryonic stem cells, with BHK, HeK or Hela cells as preferred cells. Eukaryotic cells are, preferably, used for the expression of the recombinant gene by applying the transcriptional regulation sequence or the expression vector of the present invention.

Another aspect of the present invention relates to a method for obtaining the fusion protein of the invention, hereinafter first method of the invention, comprising:

a) culturing the host cell of the invention under conditions that allow for the production of the fusion protein of the invention; and b) recovering and purifying the fusion protein produced in step (a) above.

A host cell culture refers to the process of maintaining and growing host cells. Cell cultures need controlled conditions of temperature, pH, percentages of gases (oxygen and carbon dioxide), as well as the presence of suitable nutrients to allow for cell viability and division. Cell cultures can be grown on solid substrates such as agar, or in liquid medium, which allows large numbers of cells to be cultured in suspension.

The term "purify" as used in the description refers to the isolation of the fusion protein of the invention and its concentration, of the rest of the polypeptides present in the culture medium, and of the host cell of the invention. The isolation of the polypeptide of the invention can be carried out by differential solubility, chromatography, electrophoresis or isoelectric focusing techniques. Chromatography techniques can be based on molecular weight, ionic charge (based on the ionization state of amino acids under working conditions), the affinity of the protein for certain chromatographic columns or matrices, or by means of purification tags, and it can be carried out in a column, on paper or on a plate. The protein can be isolated, for example, by precipitation with ammonium sulphate, fast protein liquid chromatography (FPLC) or high performance liquid chromatography (HPLC), using automated systems that significantly reduce the purification time and increase purification performance. The expression "purification tag" or "affinity tag", as used herein, refers to an amino acid sequence that has been incorporated (generally, by genetic engineering) into a protein to facilitate its purification. The tag, which can be another protein or a short amino acid sequence, allows for protein purification, for example, by affinity chromatography. Purification tags known in the state of the art are, for example, but not limited to, calmodulin-binding peptide (CBP), glutathione-S-transferase (GST) enzyme or a tail of histidine residues.

In another aspect, the present invention relates to a composition, hereinafter composition of the invention, which comprises the fusion protein, the nucleic acid, the plasmid, or the host cell of the invention, and at least one excipient and/or carrier.

In another aspect, the present invention relates to the fusion protein, the nucleic acid, the vector or the composition of the invention for use as a medicament.

From here, all information mentioned in relation to the medical uses of the different aspects of the invention: the fusion protein, the nucleic acid, the vector or the composition of the invention, indistinctly refer to all of them, although only the composition of the invention is mentioned.

The term "medicament", as used in this specification, refers to any substance used for the prevention, diagnosis, alleviation, treatment or cure of diseases in humans and animals. For purposes of the present invention, the terms "medicament", "pharmaceutical composition", or "veterinary composition" are used as synonyms.

In a preferred embodiment, the composition of the invention is a medicament for veterinary use, more preferably for use in aquatic animals, even more preferably for use in fish, and more preferably, in fish of the salmonid family.

"Aquatic animal", as used herein, includes any multicellular organism that lives in water, typically fish. Preferably, said aquatic animal is an animal belonging to a fish species cultivated by means of aquaculture. Illustrative examples of said aquatic animals include teleost fish, such as vertebrate fish, for example, salmonids (e.g., trout, salmon, etc.), carp, turbot, sea bream, seabass, etc.

In a preferred embodiment, the aquatic animals are preferably animals belonging to the salmonid family. The term "salmonid family" within the scope of this invention shall be understood to include all representatives of the family Salmonidae, especially of the subfamily Salmoninae and, preferably, the following species: Rainbow trout (*Oncorhynchus mykiss*); Chinook salmon (*Oncorhynchus tshawytscha*); Coho salmon (*Oncorhynchus kisutch*); Atlantic salmon (*Salmo salar*); Common trout (*Salmo trutta*); grayling (*Thymallus thymallus*); whitefish (*Coregonus* spp.); Chum salmon (*Oncorhynchus keta*); Sockeye salmon (*Oncorhynchus nerka*); Lake trout (*Salvelinus namaycush*); Brook trout (*Salvelinus fontinalis*); Arctic char (*Salvelinus alpinus*). In a more particular embodiment, the aquatic animals are preferably Rainbow trout (*Oncorhynchus mykiss*) and Common trout (*Salmo trutta*).

The compositions of this invention, as well as the other aspects of the invention mentioned above, fusion protein, nucleic acids that encode the fusion protein of the invention, and the plasmid of the invention, are suitable for treating myxozoic parasitic diseases of economic importance in farmed fish species, including *Kudoa* spp., *Ceratomyxa* spp., *Parvicapsula* spp., *Myxobolus* spp., *Tetracapsuloides* spp., inter alia; they are preferably suitable for treating parasitic diseases caused by pathogens of the genus *Tetracapsuloids* spp., preferably by the species *T. bryosalmonae*. Said compositions are also useful for the treatment of the red mark syndrome.

Thus, another aspect of the present invention relates to the composition of the invention for its use in the treatment and/or prevention of inflammatory diseases in aquatic animals, preferably diseases that cause B-cell mediated inflammation, preferably the red mark syndrome or PKD disease, the latter caused by parasites of the genus *Tetracapsuloids*, more preferably by *T. bryosalmonae*.

In a more preferred embodiment, the aquatic animals are preferably fish, more preferably fish of the salmonid family, as described earlier. In a more preferred embodiment, the aquatic animal is the Rainbow trout.

In another more preferred embodiment, the parasite of the genus *Tetracapsuloids* spp. is preferably the species *T. bryosalmonae*.

The term "treatment" as understood in the present invention refers to combating the effects caused as a result of a disease or pathological condition of interest in a subject, preferably an aquatic animal, more preferably, a fish, which includes:

(i) inhibiting the disease or pathological condition, in other words, stopping its development;

(ii) alleviating the disease or the pathological condition, in other words, causing the remittance of the disease or pathological condition or the symptoms thereof;

(iii) stabilizing the disease or pathological condition.

The composition or medicament to which the present invention relates is preferably for veterinary use. The medicament or composition for veterinary use is any substance or combination of substances that has curative or preventive properties with respect to animal diseases or that can be administered to an animal for the purpose of restoring, correcting or modifying its physiological functions exerting a pharmacological, immunological or metabolic effect, or establishing a veterinarian diagnosis. "Veterinary medicines" will also be considered "premixes for medicated feed" prepared to be incorporated into a feed.

Optionally, the medicament of the present invention comprises, at least, a carrier and/or an acceptable excipient. The term "excipient" refers to a substance that aids the absorption of any of the components of the composition of the present invention, stabilizes said components or aids the preparation of the composition in the sense of giving it consistency or providing flavours that make it more pleasant. Thus, excipients could have the function of holding components together, such as starches, sugars or celluloses, the function of sweetening, the function of colouring, the function of protecting the medicament, for example to isolate it from air and/or moisture, the function of filling a tablet, capsule or any other form of presentation such as dibasic calcium phosphate, the function of disintegrating in order to facilitate the dissolution of components and the absorption thereof in the intestine, without excluding other types of excipients not mentioned herein. Therefore, the term "excipient" is defined as a material that, included in "galenic forms", is added to active ingredients or to the associations thereof to allow for the preparation and stability thereof, to modify the organoleptic properties thereof or to determine the physicochemical properties of the pharmaceutical or veterinary composition and the bioavailability thereof.

The "carrier" or vehicle is preferably an inert substance. The function of the carrier is to facilitate the incorporation of other compounds, allow better dosing and administration or give the pharmaceutical composition consistency and shape. Therefore, the carrier is a substance that is used in the medicament or pharmaceutical or veterinary composition to dilute any of the components thereof to a certain volume or weight; or that, even without diluting said components, it is capable of allowing better dosing and administration or giving the medicament or composition consistency and shape. When the form of presentation is liquid, the pharmaceutically acceptable carrier is the diluent.

Moreover, the excipient and the carrier must be pharmacologically or veterinarily acceptable, in other words, the excipient and the carrier are allowed and evaluated so that no harm is caused to the organisms to which it is administered.

The composition of the invention will contain a prophylactically or therapeutically effective amount of the fusion protein, nucleic acid or plasmid of the invention, to provide the desired therapeutic effect. As used herein, the term "effective amount" refers to the amount of the fusion protein, nucleic acid, or plasmid of the invention contained in the composition that is capable of producing the desired therapeutic effect. In general, the effective amount to be administered will depend, among other factors, on the subject's own characteristics, the severity of the disease, the form of administration, etc. For this reason, the doses mentioned in this invention should be taken only as a guide for the person skilled in the art, who should adjust this dose depending on the factors described above.

In each case, the form of presentation of the medicament or composition will be adapted to the type of administration used; to that end, the composition of the present invention can be presented in the form of solutions or any other form of administration that is veterinarily permitted and in a therapeutically effective amount. Thus, the composition can be presented in a form adapted for oral, sublingual, nasal, intrathecal, intramuscular, bronchial, lymphatic, rectal, transdermal or inhaled administration, but without being limited to these forms. As understood by a person skilled in the art, sometimes the direct administration of the composition or plasmid of the invention to the site that is to be helped can be advantageous. In this manner, the direct administration of the composition or the plasmid of the invention to the desired organ or tissue can be achieved by direct administration (by injection, etc.) on the external surface of the affected organ or tissue by inserting a suitable device, e.g., an appropriate cannula, by arterial or venous perfusion (including retrograde flow mechanisms) or by other means mentioned in this description or known in the art.

In a preferred embodiment, the administration of the composition or plasmid of the invention is an intramuscular administration.

The composition of the invention will be formulated according to the chosen form of administration. Thus, the composition of the invention can be prepared in a liquid dosage form, for example, in the form of a solution or suspension, to be injected or perfused to the individual, preferably the aquatic animal as defined above.

In another aspect, the present invention relates to a method of treatment and/or prevention of inflammatory diseases in aquatic animals that comprises the administration of a therapeutically effective amount of the fusion protein, nucleic acid, plasmid, or composition of the invention.

In a more particular embodiment of the method of treatment and/or prevention of the invention, it is characterized in that the aquatic animals belong to the salmonid family and are selected from the list that consists of: Rainbow trout (*Oncorhynchus mykiss*); Chinook salmon (*Oncorhynchus tshawytscha*); Coho salmon (*Oncorhynchus kisutch*); Atlantic salmon (*Salmo salar*); Common trout (*Salmo trutta*); Grayling (*Thymallus thymallus*); Whitefish (*Coregonus* spp.); Chum salmon (*Oncorhynchus keta*); Sockeye salmon (*Oncorhynchus nerka*); Lake trout (*Salvelinus namaycush*); Brook trout (*Salvelinus fontinalis*) and Arctic char (*Salvelinus alpinus*). In another more particular embodiment, the salmonids are Rainbow trout (*Oncorhynchus mykiss*) and Common trout (*Salmo trutta*).

In another more particular embodiment, the inflammatory diseases that can affect salmonid species from the foregoing list comprise Proliferative Kidney Disease, caused by parasites of the genus *Tetracapsuloids*, preferably by *T. bryosalmonae*, and the red mark syndrome.

Effective dosages and administration schedules of the compositions comprising the fusion protein, nucleic acid, plasmid, or composition of the invention described herein can be determined empirically and making such determinations is within the skill in the art. Dosage ranges for the administration of the compositions are those wide enough to produce the desired effect. The dosage should not be so high as to cause adverse side effects, such as unwanted cross-reactions, anaphylactic reactions, and the like. The dosage may vary and can be administered in one or more daily dose administrations, for one or several days.

Throughout the description and the claims, the word "comprises" and its variants do not intend to exclude other technical features, additives, components or steps. For those skilled in the art, other objects, advantages and features of the invention may be partially deduced from both the description and the embodiment of the invention. The following examples and figures are provided by way of illustration and are not intended to limit the present invention.

EXAMPLES

Figure 1:
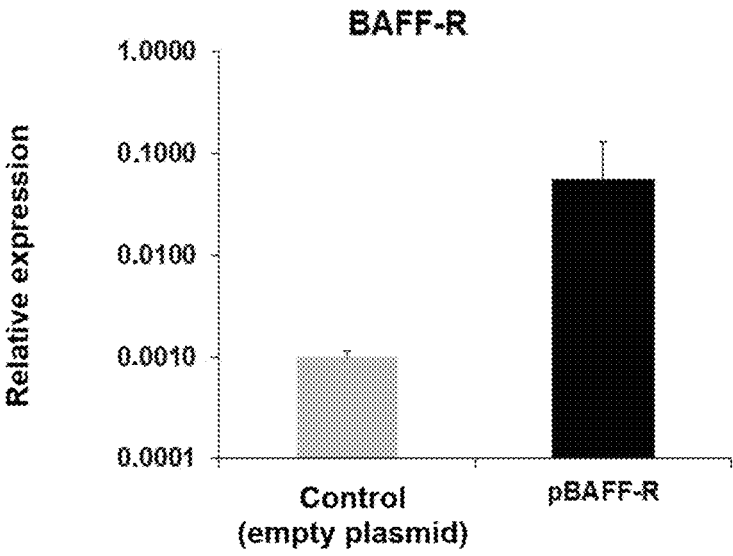
FIG. 1. Transcription levels of the gene that encodes the extracellular domain of the Rainbow trout BAFF receptor (BAFF-R) after intramuscular injection of the pBAFF-R plasmid. At day 7 post-injection, the fish were sacrificed to sample the muscle of the dorsal area and determine the levels of gene expression by real-time PCR. The empty plasmid without the gene construct was used as a negative control. The data is shown as the relative expression of each gene compared to the expression of the endogenous control gene EF-1α (mean+SD; n=3-6).

Next, the invention will be illustrated by means of assays carried out by the inventors that demonstrate the effectiveness of the product of the invention.

Example 1. Obtaining the pBAFF-R Plasmid (SEQ ID NO: 11) Encoding the IL-2-BAFF-R Fusion Protein (SEQ ID NO: 8)

The nucleotide sequence (SEQ ID NO: 3) that encodes the extracellular domain of BAFF-R (SEQ ID NO: 4) from Rainbow trout was fused to the nucleotide sequence (SEQ ID NO: 1) that encodes the Rainbow trout IL-2 signal peptide (SEQ ID NO: 2) giving rise to the IL-2-BAFF-R construct comprising the nucleotide sequence SEQ ID NO: 7 that encodes the IL-2-BAFF-R fusion protein comprising the amino acid sequence SEQ ID NO: 8.

To allow further purification of the IL-2-BAFF-R construct, the nucleotide sequence (SEQ ID NO: 5) that encodes the Fc region of the mouse IgG1 immunoglobulin-like domain (SEQ ID NO: 6) was fused thereto, giving rise to the IL-2-BAFF-R-IgG1 construct which comprises the nucleotide sequence SEQ ID NO: 9, which encodes the amino acid sequence SEQ ID NO: 10.

Thus, the foregoing construct was cloned into the pcDNA3.1+ eukaryotic expression vector (Invitrogen), previously digested by HindIII/XhoI restriction enzymes. Next, said plasmid, called pBAFF-R (SEQ ID NO: 11), was transformed into JM109 *E. coli* competent cell bacteria (Promega) following the manufacturer's instructions. Transformed colonies were selected on LB agar medium (Invitrogen) supplemented with ampicillin (100 µg/ml) for subsequent plasmid extraction and purification (Invitrogen).

Subsequently, the nucleotide sequence of the cloned pBAFF-R plasmid was confirmed by sequencing using the T7 primer (SEQ ID NO: 12; 5'-TAATACGACTCAC-TATAGGG-3') derived from the vector.

The empty plasmid without the nucleotide sequence that encodes the IL-2-BAFFR-IgG1 gene construct was used as a negative control.

Example 2. Study of BAFF-R Transcription after Intramuscular Injection of pBAFF-R (SEQ ID NO: 11)

Rainbow trout (*Oncorhynchus mykiss*) of 7 cm supplied by the Cifuentes fish farm (Guadalajara, Spain) were used. To that end, the fish were kept at the Animal Health Research Centre (CISA-INIA) at 14° C. and fed daily with a commercial diet (Skretting, Norway). Before starting the experiments, the fish were acclimatised to laboratory conditions for 2 weeks.

The fish were divided into two groups and injected intramuscularly with 1 µg of pBAFF-R plasmid resuspended in 50 µl of sterile saline solution (0.9% NaCl) or with the same amount of empty plasmid (negative control). The fish were sacrificed 7 days post-injection and a sample was taken from the muscle area of each fish where the injection had been made for RNA extraction.

The total muscle RNA was extracted using Tri-reagent (Invitrogen), following the manufacturer's instructions and stored at –80° C. until use. The purified RNA was quantified using the Nanodrop 1000 spectrophotometer (Thermo Scientific). Next, 1 µg of RNA was treated with the DNase I enzyme using the RapidOut DNA Removal Kit (Thermo Scientific) to remove traces of genomic DNA and it was used to synthesise cDNA with the RevertAid Reverse Transcriptase enzyme (Thermo Scientific) and oligo(dT)23VN (1.6 µM), as indicated by the manufacturer. The resulting cDNA was diluted to 1:5 with nuclease-free water and stored at –20° C. until use.

The expression levels of the extracellular domain of BAFF-R were analysed by real-time PCR using the Light-Cycler 96 System instrument (Roche). All amplification reactions were performed in duplicate using the FastStart Essential DNA Green Master reaction mix (Roche) and specific primers (Table 1). The amplification conditions consisted of an initial denaturation step (95° C., 10 minutes), followed by 40 cycles of amplification (95° C. for 10 s, 60° C. for 10 s and 72° C. for 10 s). Moreover, a dissociation curve was obtained by reading the fluorescence signal every degree between the temperatures 60° C. and 95° C. to verify that this signal is due to the amplification of a single product. Negative controls without template DNA and negative reverse transcription (RT–) controls were included in all assays. The expression of the extracellular domain of the BAFF-R receptor was normalised with the expression of the gene that encodes the Rainbow trout elongation factor-1α

(EF-1α) (Montero, J., J. et al., J. Virol. 2011; 85:4046-4056) which is constitutively expressed in all organs to the same extent, using specific primers (Table 1). The expression levels were calculated with the 2-ΔCt method, wherein ΔCt was determined by subtracting the Ct value of EF-1α from the Ct value of the target gene (Livak, K. J., and T. D. Schmittgen. Methods. 2001; 25:402-408). Statistical analysis was performed using a two-tailed Student's t-test with Welch's correction and the differences were considered statistically significant when $p < 0.05$.

TABLE 1

| List of primers used in transcriptional studies. | | |
| --- | --- | --- |
| Gene | Forward primer (5'-3') | Reverse primer (5'-3) |
| EF-1α | SEQ ID NO: 13 (gatccagaagga ggtcacca) | SEQ ID NO: 14 (ttacgttcgacc ttccatcc) |
| BAFF-R | SEQ ID NO: 15 (gacaaactgctc atcacctgtatc) | SEQ ID NO: 16 (atatccagacag ctggactcactg) |
| 18S rRNA *T. bryosalmonae* | SEQ ID NO: 17 (ggacactgcatg tgctgcatagt) | SEQ ID NO: 18 (ccatgctagaat gtccaggcact) |

As can be seen in FIG. 1, after intramuscular injection of the pBAFF-R plasmid, an increase in BAFF-R mRNA expression was detected in the muscle (56 times higher) compared to the expression shown by the trout treated with the empty plasmid (negative control).

Example 3. Obtaining Supernatants with the Extracellular Domain of the Rainbow Trout BAFF Receptor (BAFF-R)

To verify that the pBAFF-R plasmid of the invention is capable of effectively transcribing and translating the extracellular domain of Rainbow trout BAFF-R, EPC (*Epithelioma papulosum* cyprinid) cells were transfected with said pBAFF-R plasmid using the 4D-Nucleofector™ kit (Lonza). To that end, the EPC cells maintained in Leibovitz medium (L-15, Life Technologies) supplemented with penicillin (100 units/ml, Life Technologies), streptomycin (100 µg/ml, Life Technologies) and foetal bovine serum (10% FBS, Life Technologies) were trypsinised and transfected with 1 µg of plasmid pBAFF-R using the reagents of the Amaxa P3 Primary cell kit (Lonza). Next, the transfected cells were cultured in 24-well plates at a concentration of $5 \times 10^5$ cells/ml. After 24 h of incubation at 20° C., the culture medium was changed using L-15 medium supplemented with antibiotics and 0.1% FBS. After incubating the cells for another 24 h, the supernatants were collected from the wells and concentrated (50×) using 3 kDa molecular-weight cutoff centricons (GE Healthcare Life Sciences). In addition, the culture supernatants of the EPC cells transfected with the empty plasmid (negative control) were also collected. In order to verify the correct transfection of the cells, the pmaxGFP plasmid supplied in the Amaxa kit was used as a positive control for the subsequent visualisation of the green fluorescent protein by fluorescence microscopy (Zeiss Axio Vert.A1).

The concentrated supernatants of the EPC cells transfected with the pBAFF-R plasmid of the invention and with the empty plasmid were analyzed by polyacrylamide gel electrophoresis (SDS-PAGE, sodium dodecyl sulfate-polyacrylamide gel electrophoresis). To that end, the polyacrylamide gel (12%; Bio-Rad) was loaded with 20 µl of concentrated supernatant under reducing conditions and stained with Coomassie blue. Protein transfer was carried out on a polyvinylidene fluoride membrane (PVDF; Bio-Rad) using the Trans-Blot Turbo kit (Bio-Rad) to identify the protein corresponding to the extracellular domain of the Rainbow trout BAFF receptor (BAFF-R) by Western blot. To that end, the membrane was blocked with 5% skim milk in phosphate-buffered saline (PBS) at room temperature for 1 h. Then, the membrane was incubated with a rabbit anti-mouse IgG primary antibody (Sigma-Aldrich) and prepared in the blocking solution at 4° C. for 16 h. The membrane was then washed three times with 0.1% Tween 20 (Sigma-Aldrich) prepared in PBS for 10 min and incubated with a horseradish peroxidase-conjugated donkey anti-rabbit IgG secondary antibody (GE Healthcare Life Sciences) at room temperature for 1 h. After three washes in 0.1% Tween 20-PBS and a final wash in PBS, the membrane was revealed by peroxidase chemiluminescent reaction using the ECL kit (GE Healthcare Life Sciences).

Figure 2:
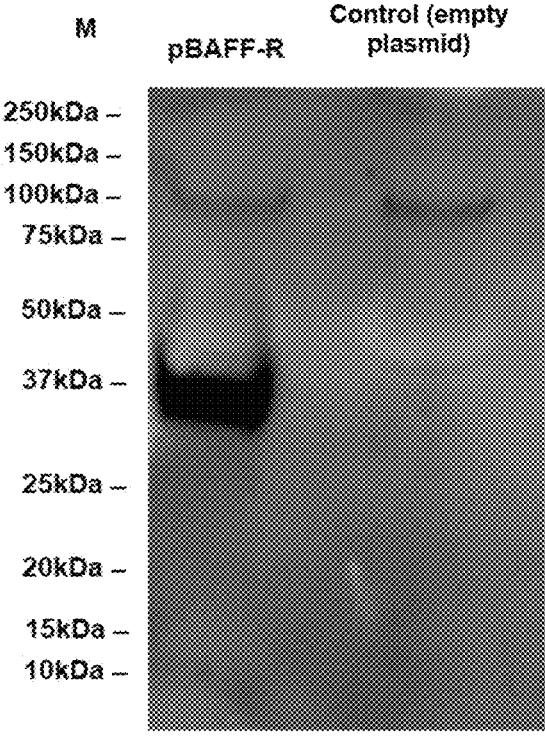
FIG. 2. Protein corresponding to the extracellular domain of the Rainbow trout BAFF receptor (BAFF-R) detected by the western blot technique using the concentrated supernatant of EPC cells transfected with the pBAFF-R plasmid. The empty plasmid without the gene construct was used as a negative control. M, marker.

As can be seen in FIG. 2, the protein corresponding to the extracellular domain of BAFF-R was detected, showing a specific band of 37 kDa.

Example 4. The Administration of the pBAFF-R Plasmid (SEQ ID NO: 11) Reduces the Degree of Posterior Kidney Inflammation and Mortality in Trout Naturally Infected by *T. bryosalmonae*

Forty-four 30-40 g trout from the Southampton fish farm (United Kingdom) were used, free from infection by *T. bryosalmonae* and divided into two groups (20-24 fish per group). The fish of one of the groups were treated with two intramuscular injections (front and back of the dorsal fin) of the pBAFF-R plasmid (10 µg) dissolved in 20 µl of phosphate buffer (PBS) (20 µg of the pBAFF-R plasmid administered in total per fish). The fish of the second group were treated in the same way, but instead of administering the pBAFF-R plasmid, they were only administered the same volume of phosphate buffer (PBS) without plasmid.

Next, both groups of animals were introduced into a fish farm where an outbreak of PKD had been detected (Test Valley Trout), recording at each moment the number of dead fish. This assay was carried out in the middle of May, when the water temperature increased, reaching values higher than 15° C. At 90 days post-injection, when the temperature was still above 15° C. and the outbreak of PKD persisted on the farm, the trout were sacrificed to analyze the level of posterior kidney inflammation and thus determine the degree of infection by the parasite. The statistical analysis was performed using the Mann-Whitney nonparametric test and the differences were considered statistically significant for p<0.05.

Figure 3:
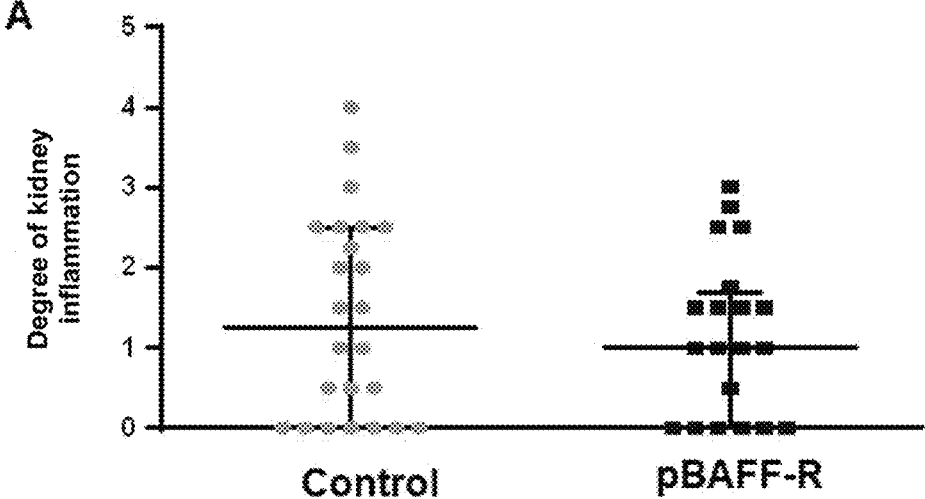
FIG. 3. Effect of intramuscular treatment with the pBAFF-R plasmid in Rainbow trout naturally infected with *T. bryosalmonae*. (A) Degree of posterior kidney inflammation of trout treated with the pBAFF-R plasmid (n=20) or PBS (negative control; n=24). The individual value plot shows the interquartile range and the median of the data. (B) Percentage of trout affected or killed by PKD after intramuscular injection of the pBAFF-R plasmid or PBS (control).
Figure 3:
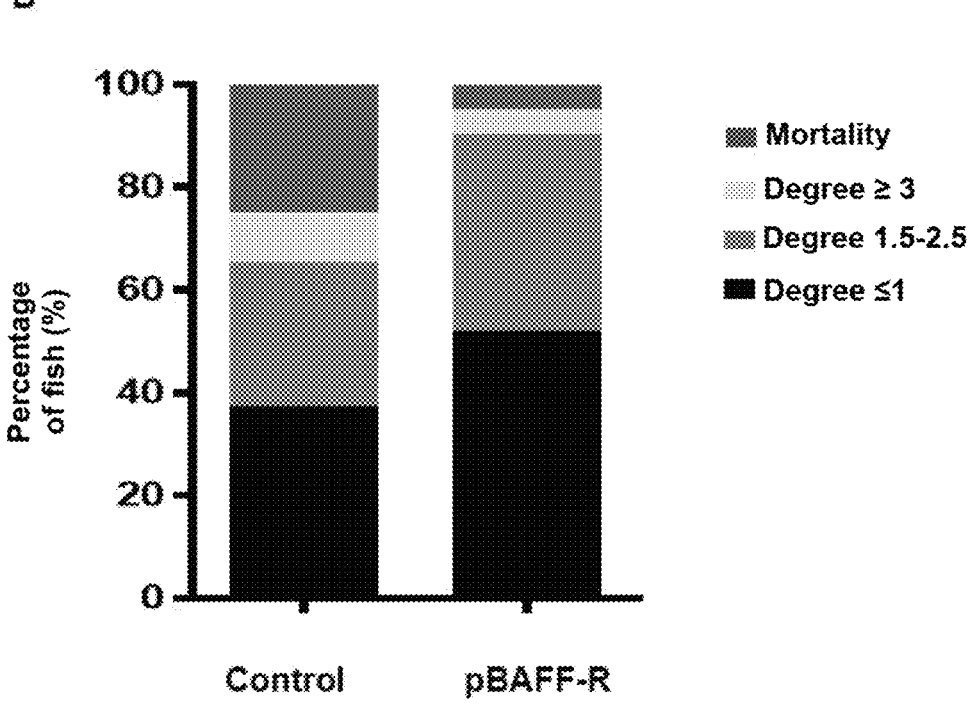

The results show that the intramuscular administration of the pBAFF-R plasmid in trout produced a decrease in the degree of kidney inflammation caused by PKD infection compared to the degree of kidney inflammation shown by the control group (FIG. 3A).

The percentage of mortality presented by both groups of animals was also analyzed, showing that said percentage of mortality was lower in the group of trout treated with the pBAFF-R plasmid (4.76%) compared to the percentage shown by the control group (25%) (FIG. 3B). Moreover, as shown in FIG. 3B, the percentage of trout that presented a degree of mortality ≤1 was greater (52.38%) in the group treated with the pBAFF-R plasmid than in the control group (37.50%).

Example 5. The Administration of the pBAFF-R Plasmid (SEQ ID NO: 11) Reduces the Load of *T. bryosalmonae* in Trout Naturally Infected by this Parasite To determine whether the administration of the pBAFF-R plasmid is capable of modifying the long-term parasite load in trout naturally infected with *T. bryosalmonae* and that manage to survive the disease, the pBAFF-R plasmid was injected intramuscularly into the fish to carry out transcriptional studies of the 18S rRNA gene of *T. bryosalmonae*. Due to the marked seasonality of this parasitic disease, the treatment with the pBAFF-R plasmid was carried out during the month of July when an outbreak of PKD was detected, when cases of mortality associated with the characteristic symptoms of this disease appeared and, moreover, the temperature of the water at the fish farm was above 15° C.

Forty 30-40 g Rainbow trout were used from the Cifuentes fish farm (Guadalajara, Spain) and were divided into four groups (10 fish per group). Each fish was injected intramuscularly with 100 µl of sterile saline solution (0.9% NaCl) containing 0.1 or 1 µg of the pBAFF-R plasmid (two groups), as well as 0.1 or 1 µg of the empty plasmid without the construct in two other groups (negative controls). The fish of each group were sacrificed 110 days post-injection, in the month of November when the water temperature was below 15° C. and the outbreak of PKD had subsided at the fish farm. As expected, inflammation of the kidney was not observed in any case. A posterior kidney sample was taken from each trout for RNA extraction with Tri-reagent and subsequent cDNA synthesis using the methodology explained above in Example 2 was carried out.

Figure 4:
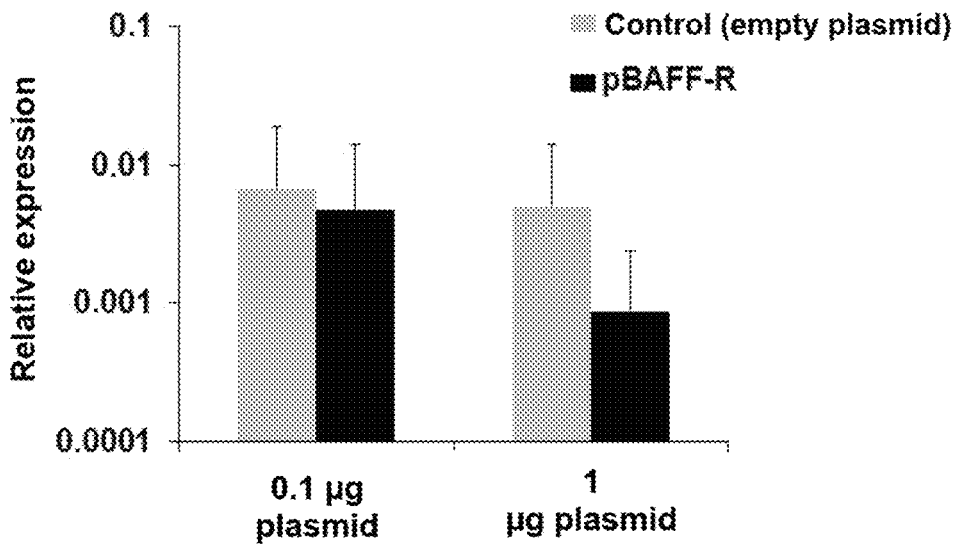
FIG. 4. Transcription levels of 18S rRNA from *T. bryosalmonae* after intramuscular injection of the plasmid (0.1 and 1 μg) containing the sequence of the extracellular domain of the BAFF receptor (pBAFF-R) in Rainbow trout naturally infected by *T. bryosalmonae*. At day 110 post-injection, the fish were sacrificed to sample the posterior kidney and determine the expression levels of the 18S rRNA gene of *T. bryosalmonae* by real-time PCR. The empty plasmid without the gene construct was used as a negative control. The data is shown as the relative expression of each gene compared to the expression of the endogenous control gene EF-1α (mean+SD; n=5-7).

The results show that the administration of a dose of 0.1 µg of the pBAFF-R plasmid did not induce a decrease in the expression of the 18S rRNA gene of *T. bryosalmonae* in the posterior kidney at 110 days post-injection (FIG. 4). However, when a dose of 1 µg of the pBAFF-R plasmid was administered, a decrease in the parasite load detected in the kidney at the transcriptional level was observed (FIG. 4).

Thus, these results indicate that the administration of the plasmid of the invention is capable of favouring the specific immune response of the infected organism against the parasite and its elimination from the organism, as well as controlling B-cell mediated inflammation of the kidney tissue, thus favouring the survival and symptoms of the infection caused by *T. bryosalmonae*, in Rainbow trout.

The invention claimed is:

1. A fusion protein comprising an amino acid sequence comprising at least 95% identity to SEQ ID NO: 10 that comprises a first amino acid sequence comprising an inter-leukin (IL-2) signal peptide fused to a second amino acid sequence corresponding to an extracellular domain of the BAFF receptor (B-cell activating factor receptor, BAFF-R), wherein the signal peptide directs the extracellular domain of the fusion protein to BAFF, which fusion protein binds to BAFF and inhibits BAFF-mediated signaling.

2. A composition comprising the fusion protein according to claim 1, and at least one of: an excipient and a carrier.

3. The composition according to claim 2, characterized in that it is a pharmaceutical or veterinary composition.

4. A fusion protein comprising a first amino acid sequence comprising the interleukin-2 (IL-2) signal peptide of SEQ ID NO: 2 fused to a second amino acid sequence comprising at least 95% identity to the extracellular domain of the BAFF receptor (B-cell activating factor receptor, BAFF-R) of SEQ ID NO: 4; wherein the fusion protein comprises at least 95% identity to SEQ ID NO: 10 and the signal peptide directs the extracellular domain of the fusion protein to BAFF, which fusion protein binds to BAFF and inhibits BAFF-mediated signaling.

5. A nucleic acid encoding the fusion protein according to claim 1.

6. The nucleic acid according to claim 5, comprising a sequence with at least 95% identity to any of SEQ ID NO: 7 or SEQ ID NO: 9.

7. A plasmid comprising a nucleic acid molecule accord-ing to claim 5, wherein, at least one of:
   a) the nucleic acid molecule is operably bonded to an expression control sequence suitable for expression in a host cell; and
   b) the plasmid comprises one or more selectable marker genes.

8. The plasmid according to claim 7, characterized in that it comprises SEQ ID NO: 11.

9. A host cell comprising a nucleic acid molecule accord-ing to claim 5.

10. A composition comprising the nucleic acid according to claim 5, and at least one of: an excipient and a carrier.

11. A method for the treatment, whether prophylactic or therapeutic, of one or more inflammatory diseases in a salmonid animal that comprises the administration of a therapeutically effective amount of the fusion protein according to claim 1 to salmonid animal in need thereof.

12. The method according to claim 11 wherein the administration is by intramuscular route.

13. The method of claim 11, wherein the one or more inflammatory diseases are caused by myxozoans of the genus *Tetracapsuloides.*

14. The method according to claim 11, wherein the one or more inflammatory diseases are Proliferative Kidney Disease and the Red Mark Syndrome.

15. The method according to claim 11, wherein the salmonid animal is selected from the list consisting of: Rainbow trout (*Oncorhynchus mykiss*); Chinook salmon (*Oncorhynchus tshawytscha*); Coho salmon (*Oncorhynchus kisutch*); Atlantic salmon (*Salmo salar*); Common trout (*Salmo trutta*); Grayling (*Thymallus thymallus*); Whitefish (*Coregonus* spp.); Chum salmon (*Oncorhynchus keta*); Sockeye salmon (*Oncorhynchus nerka*); Lake trout (*Salvelinus namaycush*); Brook trout (*Salvelinus fontinalis*) and Arctic char (*Salvelinus alpinus*).

16. The method according to claim 11, wherein the salmonid animal is one of Rainbow trout (*Oncorhynchus mykiss*) and Common trout (*Salmo trutta*).

\* \* \* \* \*

SEQUENCE LISTING

<160> NUMBER OF SEQ ID NOS: 18

<210> SEQ ID NO 1
<211> LENGTH: 60
<212> TYPE: DNA

-continued

<213> ORGANISM: Artificial Sequence
<220> FEATURE:
<223> OTHER INFORMATION: Coding sequence of the rainbow trout IL-2
      signal peptide

<400> SEQUENCE: 1
atggaccgtc gttacaggat ttccttttg acgctttttc tcaccggttg tctacaagga      60

<210> SEQ ID NO 2
<211> LENGTH: 20
<212> TYPE: PRT
<213> ORGANISM: Artificial Sequence
<220> FEATURE:
<223> OTHER INFORMATION: Rainbow trout IL-2 signal peptide

<400> SEQUENCE: 2

Met Asp Arg Arg Tyr Arg Ile Ser Phe Leu Thr Leu Phe Leu Thr Gly
1               5                   10                  15

Cys Leu Gln Gly
            20

<210> SEQ ID NO 3
<211> LENGTH: 165
<212> TYPE: DNA
<213> ORGANISM: Artificial Sequence
<220> FEATURE:
<223> OTHER INFORMATION: Extracellular domain of the rainbow trout
      BAFF-R

<400> SEQUENCE: 3
atggcaaaga agacctgtga tccgggcaca agttgggaca aactgctcat cacctgtatc     60
cccttgacaa ggccaaagcc agccacagaa tccccacctg taaaatggag tagcgacgtt    120 cctcccagt acgacccggc agtgagtcca gctgtctgga tatca                     165

<210> SEQ ID NO 4
<211> LENGTH: 55
<212> TYPE: PRT
<213> ORGANISM: Artificial Sequence
<220> FEATURE:
<223> OTHER INFORMATION: Extracellular domain of the rainbow trout
      BAFF-R

<400> SEQUENCE: 4

Met Ala Lys Lys Thr Cys Asp Pro Gly Thr Ser Trp Asp Lys Leu Leu
1               5                   10                  15

Ile Thr Cys Ile Pro Leu Thr Arg Pro Lys Pro Ala Thr Glu Ser Pro
            20                  25                  30

Pro Val Lys Trp Ser Ser Asp Val Pro Pro Gln Tyr Asp Pro Ala Val
        35                  40                  45

Ser Pro Ala Val Trp Ile Ser
    50                  55

<210> SEQ ID NO 5
<211> LENGTH: 669
<212> TYPE: DNA
<213> ORGANISM: Artificial Sequence
<220> FEATURE:
<223> OTHER INFORMATION: Fc domain of mouse IgG1

<400> SEQUENCE: 5
ggttgtaagc cttgcatatg tacagtccca gaagtatcat ctgtcttcat cttccccca      60 aagcccaagg atgtgctcac cattactctg actcctaagg tcacgtgtgt tgtggtagac    120

```
atcagcaagg atgatcccga ggtccagttc agctggtttg tagatgatgt ggaggtgcac        180
acagctcaga cgcaacccg ggaggagcag ttcaacagca ctttccgctc agtcagtgaa        240
cttcccatca tgcaccagga ctggctcaat ggcaaggagt tcaaatgcag ggtcaacagt        300
gcagctttcc ctgcccccat cgagaaaacc atctccaaaa ccaaaggcag accgaaggct        360
ccacaggtgt acaccattcc acctcccaag gagcagatgg ccaaggataa agtcagtctg        420
acctgcatga taacagactt cttccctgaa gacattactg tggagtggca gtggaatggg        480
cagccagcgg agaactacaa gaacactcag cccatcatgg acacagatgg ctcttacttc        540
gtctacagca agctcaatgt gcagaagagc aactgggagg caggaaatac tttcacctgc        600
tctgtgttac atgagggcct gcacaaccac catactgaga agagcctctc ccactctcct        660
ggtaaatga                                                              669
```

```
<210> SEQ ID NO 6
<211> LENGTH: 222
<212> TYPE: PRT
<213> ORGANISM: Artificial Sequence
<220> FEATURE:
<223> OTHER INFORMATION: Fc domain of mouse IgG1

<400> SEQUENCE: 6

Gly Cys Lys Pro Cys Ile Cys Thr Val Pro Glu Val Ser Ser Val Phe
1               5                   10                  15

Ile Phe Pro Pro Lys Pro Lys Asp Val Leu Thr Ile Thr Leu Thr Pro
                20                  25                  30

Lys Val Thr Cys Val Val Val Asp Ile Ser Lys Asp Asp Pro Glu Val
            35                  40                  45

Gln Phe Ser Trp Phe Val Asp Asp Val Glu Val His Thr Ala Gln Thr
        50                  55                  60

Gln Pro Arg Glu Glu Gln Phe Asn Ser Thr Phe Arg Ser Val Ser Glu
65                  70                  75                  80

Leu Pro Ile Met His Gln Asp Trp Leu Asn Gly Lys Glu Phe Lys Cys
                85                  90                  95

Arg Val Asn Ser Ala Ala Phe Pro Ala Pro Ile Glu Lys Thr Ile Ser
                100                 105                 110

Lys Thr Lys Gly Arg Pro Lys Ala Pro Gln Val Tyr Thr Ile Pro Pro
            115                 120                 125

Pro Lys Glu Gln Met Ala Lys Asp Lys Val Ser Leu Thr Cys Met Ile
        130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
                180                 185                 190

Glu Ala Gly Asn Thr Phe Thr Cys Ser Val Leu His Glu Gly Leu His
            195                 200                 205

Asn His His Thr Glu Lys Ser Leu Ser His Ser Pro Gly Lys
        210                 215                 220
```

```
<210> SEQ ID NO 7
<211> LENGTH: 225
<212> TYPE: DNA
<213> ORGANISM: Artificial Sequence
<220> FEATURE:
<223> OTHER INFORMATION: Coding sequence of the IL2-BAFF-R construct
```

<400> SEQUENCE: 7
atggaccgtc gttacaggat ttcctttttg acgcttttc tcaccggttg tctacaagga        60
atggcaaaga agacctgtga tccgggcaca agttgggaca aactgctcat cacctgtatc       120
cccttgacaa ggccaaagcc agccacagaa tccccacctg taaaatggag tagcgacgtt       180
cctccccagt acgacccggc agtgagtcca gctgtctgga tatca                      225

<210> SEQ ID NO 8
<211> LENGTH: 75
<212> TYPE: PRT
<213> ORGANISM: Artificial Sequence
<220> FEATURE:
<223> OTHER INFORMATION: IL2-BAFF-R fusion protein

<400> SEQUENCE: 8

Met Asp Arg Arg Tyr Arg Ile Ser Phe Leu Thr Leu Phe Leu Thr Gly
1               5                   10                  15

Cys Leu Gln Gly Met Ala Lys Lys Thr Cys Asp Pro Gly Thr Ser Trp
            20                  25                  30

Asp Lys Leu Leu Ile Thr Cys Ile Pro Leu Thr Arg Pro Lys Pro Ala
        35                  40                  45

Thr Glu Ser Pro Pro Val Lys Trp Ser Ser Asp Val Pro Pro Gln Tyr
    50                  55                  60

Asp Pro Ala Val Ser Pro Ala Val Trp Ile Ser
65                  70                  75

<210> SEQ ID NO 9
<211> LENGTH: 894
<212> TYPE: DNA
<213> ORGANISM: Artificial Sequence
<220> FEATURE:
<223> OTHER INFORMATION: Coding sequence of the IL2-BAFF-R-IgG1
      construct

<400> SEQUENCE: 9
atggaccgtc gttacaggat ttcctttttg acgcttttc tcaccggttg tctacaagga        60
atggcaaaga agacctgtga tccgggcaca agttgggaca aactgctcat cacctgtatc       120
cccttgacaa ggccaaagcc agccacagaa tccccacctg taaaatggag tagcgacgtt       180
cctccccagt acgacccggc agtgagtcca gctgtctgga tatcaggttg taagccttgc       240
atatgtacag tcccagaagt atcatctgtc ttcatcttcc ccccaaagcc caggatgtg        300 ctcaccatta ctctgactcc taaggtcacg tgtgttgtgg tagacatcag caaggatgat       360
cccgaggtcc agttcagctg gtttgtagat gatgtggagg tgcacacagc tcagacgcaa       420
ccccgggagg agcagttcaa cagcactttc cgctcagtca gtgaacttcc catcatgcac       480
caggactggc tcaatggcaa ggagttcaaa tgcagggtca acagtgcagc tttccctgcc       540
cccatcgaga aaaccatctc caaaaccaaa ggcagaccga aggctccaca ggtgtacacc       600
attccacctc ccaaggagca gatggccaag ataaagtca gtctgacctg catgataaca       660
gacttcttcc ctgaagacat tactgtggag tggcagtgga atgggcagcc agcggagaac       720
tacaagaaca ctcagcccat catggacaca gatggctctt acttcgtcta cagcaagctc       780
aatgtgcaga gagcaactg ggaggcagga aatactttca cctgctctgt gttacatgag       840
ggcctgcaca accaccatac tgagaagagc ctctcccact ctcctggtaa atga            894

<210> SEQ ID NO 10

-continued

```
<211> LENGTH: 297
<212> TYPE: PRT
<213> ORGANISM: Artificial Sequence
<220> FEATURE:
<223> OTHER INFORMATION: IL2-BAFF-R-IgG1 fusion protein

<400> SEQUENCE: 10

Met Asp Arg Arg Tyr Arg Ile Ser Phe Leu Thr Leu Phe Leu Thr Gly
1               5                   10                  15

Cys Leu Gln Gly Met Ala Lys Lys Thr Cys Asp Pro Gly Thr Ser Trp
            20                  25                  30

Asp Lys Leu Leu Ile Thr Cys Ile Pro Leu Thr Arg Pro Lys Pro Ala
        35                  40                  45

Thr Glu Ser Pro Pro Val Lys Trp Ser Ser Asp Val Pro Pro Gln Tyr
    50                  55                  60

Asp Pro Ala Val Ser Pro Ala Val Trp Ile Ser Gly Cys Lys Pro Cys
65                  70                  75                  80

Ile Cys Thr Val Pro Glu Val Ser Ser Val Phe Ile Phe Pro Pro Lys
                85                  90                  95

Pro Lys Asp Val Leu Thr Ile Thr Leu Thr Pro Lys Val Thr Cys Val
            100                 105                 110

Val Val Asp Ile Ser Lys Asp Asp Pro Glu Val Gln Phe Ser Trp Phe
            115                 120                 125

Val Asp Asp Val Glu Val His Thr Ala Gln Thr Gln Pro Arg Glu Glu
    130                 135                 140

Gln Phe Asn Ser Thr Phe Arg Ser Val Ser Glu Leu Pro Ile Met His
145                 150                 155                 160

Gln Asp Trp Leu Asn Gly Lys Glu Phe Lys Cys Arg Val Asn Ser Ala
            165                 170                 175

Ala Phe Pro Ala Pro Ile Glu Lys Thr Ile Ser Lys Thr Lys Gly Arg
            180                 185                 190

Pro Lys Ala Pro Gln Val Tyr Thr Ile Pro Pro Pro Lys Glu Gln Met
            195                 200                 205

Ala Lys Asp Lys Val Ser Leu Thr Cys Met Ile Thr Asp Phe Phe Pro
    210                 215                 220

Glu Asp Ile Thr Val Glu Trp Gln Trp Asn Gly Gln Pro Ala Glu Asn
225                 230                 235                 240

Tyr Lys Asn Thr Gln Pro Ile Met Asp Thr Asp Gly Ser Tyr Phe Val
            245                 250                 255

Tyr Ser Lys Leu Asn Val Gln Lys Ser Asn Trp Glu Ala Gly Asn Thr
            260                 265                 270

Phe Thr Cys Ser Val Leu His Glu Gly Leu His Asn His His Thr Glu
            275                 280                 285

Lys Ser Leu Ser His Ser Pro Gly Lys
    290                 295

<210> SEQ ID NO 11
<211> LENGTH: 6120
<212> TYPE: DNA
<213> ORGANISM: Artificial Sequence
<220> FEATURE:
<223> OTHER INFORMATION: pBAFF-R plasmid

<400> SEQUENCE: 11
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
```

```
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttatgg accgtcgtta caggatttcc tttttgacgc tttttctcac    960
cggttgtcta caaggaatgg caaagaagac ctgtgatccg ggcacaagtt gggacaaact    1020
gctcatcacc tgtatcccct tgacaaggcc aaagccagcc acagaatccc cacctgtaaa    1080
atggagtagc gacgttcctc cccagtacga cccggcagtg agtccagctg tctggatatc    1140
aggttgtaag ccttgcatat gtacagtccc agaagtatca tctgtcttca tcttcccccc    1200
aaagcccaag gatgtgctca ccattactct gactcctaag gtcacgtgtg ttgtggtaga    1260
catcagcaag gatgatcccg aggtccagtt cagctggttt gtagatgatg tggaggtgca    1320
cacagctcag acgcaacccc gggaggagca gttcaacagc actttccgct cagtcagtga    1380
acttcccatc atgcaccagg actggctcaa tggcaaggag ttcaaatgca gggtcaacag    1440
tgcagctttc cctgccccca tcgagaaaac catctccaaa accaaaggca gaccgaaggc    1500
tccacaggtg tacaccattc cacctcccaa ggagcagatg gccaaggata aagtcagtct    1560
gacctgcatg ataacagact tcttccctga agacattact gtggagtggc agtggaatgg    1620
gcagccagcg gagaactaca agaacactca gcccatcatg gacacagatg gctcttactt    1680
cgtctacagc aagctcaatg tgcagaagag caactgggag gcaggaaata ctttcacctg    1740
ctctgtgtta catgagggcc tgcacaacca ccatactgag aagagcctct cccactctcc    1800
tggtaaatga ctcgagtcta gagggcccgt ttaaacccgc tgatcagcct cgactgtgcc    1860
ttctagttgc cagccatctg ttgtttgccc ctcccccgtg ccttccttga ccctggaagg    1920
tgccactccc actgtccttt cctaataaaa tgaggaaatt gcatcgcatt gtctgagtag    1980
gtgtcattct attctggggg gtggggtggg gcaggacagc aagggggagg attgggaaga    2040
caatagcagg catgctgggg atgcggtggg ctctatggct tctgaggcgg aaagaaccag    2100
ctggggctct aggggtatc cccacgcgcc ctgtagcggc gcattaagcg cggcgggtgt      2160
ggtggttacg cgcagcgtga ccgctacact tgccagcgcc ctagcgcccg ctcctttcgc    2220
tttcttccct tcctttctcg ccacgttcgc cggctttccc cgtcaagctc taaatcgggg    2280
gctcccttta gggttccgat ttagtgcttt acggcacctc gaccccaaaa aacttgatta    2340
gggtgatggt tcacgtagtg ggccatcgcc ctgatagacg gtttttcgcc ctttgacgtt    2400
ggagtccacg ttctttaata gtggactctt gttccaaact ggaacaacac tcaacccta     2460 ctcggtctat tcttttgatt tataagggat tttgccgatt tcggcctatt ggttaaaaaa    2520
```

-continued

```
tgagctgatt taacaaaaat ttaacgcgaa ttaattctgt ggaatgtgtg tcagttaggg    2580
tgtggaaagt ccccaggctc cccagcaggc agaagtatgc aaagcatgca tctcaattag    2640
tcagcaacca ggtgtggaaa gtccccaggc tccccagcag gcagaagtat gcaaagcatg    2700
catctcaatt agtcagcaac catagtcccg cccctaactc cgcccatccc gcccctaact    2760
ccgcccagtt ccgcccattc tccgccccat ggctgactaa ttttttttat ttatgcagag    2820
gccgaggccg cctctgcctc tgagctattc cagaagtagt gaggaggctt ttttggaggc    2880
ctaggctttt gcaaaaagct cccgggagct tgtatatcca ttttcggatc tgatcaagag    2940
acaggatgag gatcgtttcg catgattgaa caagatggat tgcacgcagg ttctccggcc    3000
gcttgggtgg agaggctatt cggctatgac tgggcacaac agacaatcgg ctgctctgat    3060
gccgccgtgt tccggctgtc agcgcagggg cgcccggttc tttttgtcaa gaccgacctg    3120
tccggtgccc tgaatgaact gcaggacgag gcagcgcggc tatcgtggct ggccacgacg    3180
ggcgttcctt gcgcagctgt gctcgacgtt gtcactgaag cgggaaggga ctggctgcta    3240
ttgggcgaag tgccggggca ggatctcctg tcatctcacc ttgctcctgc cgagaaagta    3300
tccatcatgg ctgatgcaat gcggcggctg catacgcttg atccggctac ctgcccattc    3360
gaccaccaag cgaaacatcg catcgagcga gcacgtactc ggatggaagc cggtcttgtc    3420
gatcaggatg atctggacga agagcatcag gggctcgcgc cagccgaact gttcgccagg    3480
ctcaaggcgc gcatgcccga cggcgaggat ctcgtcgtga cccatggcga tgcctgcttg    3540
ccgaatatca tggtggaaaa tggccgcttt tctggattca tcgactgtgg ccggctgggt    3600
gtggcggacc gctatcagga catagcgttg gctacccgtg atattgctga agagcttggc    3660
ggcgaatggg ctgaccgctt cctcgtgctt tacggtatcg ccgctcccga ttcgcagcgc    3720
atcgccttct atcgccttct tgacgagttc ttctgagcgg gactctgggg ttcgaaatga    3780
ccgaccaagc gacgcccaac ctgccatcac gagatttcga ttccaccgcc gccttctatg    3840
aaaggttggg cttcggaatc gttttccggg acgccggctg gatgatcctc cagcgcgggg    3900
atctcatgct ggagttcttc gcccacccca acttgtttat tgcagcttat aatggttaca    3960
aataaagcaa tagcatcaca aatttcacaa ataaagcatt tttttcactg cattctagtt    4020
gtggtttgtc caaactcatc aatgtatctt atcatgtctg tataccgtcg acctctagct    4080
agagcttggc gtaatcatgg tcatagctgt ttcctgtgtg aaattgttat ccgctcacaa    4140
ttccacacaa catacgagcc ggaagcataa agtgtaaagc ctggggtgcc taatgagtga    4200
gctaactcac attaattgcg ttgcgctcac tgcccgcttt ccagtcggga aacctgtcgt    4260
gccagctgca ttaatgaatc ggccaacgcg cggggagagg cggtttgcgt attgggcgct    4320
cttccgcttc ctcgctcact gactcgctgc gctcggtcgt tcggctgcgg cgagcggtat    4380
cagctcactc aaaggcggta atacggttat ccacagaatc aggggataac gcaggaaaga    4440
acatgtgagc aaaaggccag caaaaggcca ggaaccgtaa aaaggccgcg ttgctggcgt    4500
ttttccatag gctccgcccc cctgacgagc atcacaaaaa tcgacgctca agtcagaggt    4560
ggcgaaaccc gacaggacta taaagatacc aggcgtttcc ccctggaagc tccctcgtgc    4620
gctctcctgt tccgaccctg ccgcttaccg gatacctgtc cgcctttctc ccttcgggaa    4680
gcgtggcgct ttctcatagc tcacgctgta ggtatctcag ttcggtgtag gtcgttcgct    4740
ccaagctggg ctgtgtgcac gaaccccccg ttcagcccga ccgctgcgcc ttatccggta    4800
actatcgtct tgagtccaac ccggtaagac acgacttatc gccactggca gcagccactg    4860
```

-continued

```
gtaacaggat tagcagagcg aggtatgtag gcggtgctac agagttcttg aagtggtggc    4920
ctaactacgg ctacactaga agaacagtat ttggtatctg cgctctgctg aagccagtta    4980
ccttcggaaa aagagttggt agctcttgat ccggcaaaca aaccaccgct ggtagcggtg    5040
gtttttttgt ttgcaagcag cagattacgc gcagaaaaaa aggatctcaa gaagatcctt    5100
tgatcttttc tacggggtct gacgctcagt ggaacgaaaa ctcacgttaa gggattttgg    5160
tcatgagatt atcaaaaagg atcttcacct agatcctttt aaattaaaaa tgaagtttta    5220
aatcaatcta aagtatatat gagtaaactt ggtctgacag ttaccaatgc ttaatcagtg    5280
aggcacctat ctcagcgatc tgtctatttc gttcatccat agttgcctga ctccccgtcg    5340
tgtagataac tacgatacgg gagggcttac catctggccc cagtgctgca atgataccgc    5400
gagacccacg ctcaccggct ccagatttat cagcaataaa ccagccagcc ggaagggccg    5460
agcgcagaag tggtcctgca actttatccg cctccatcca gtctattaat tgttgccggg    5520
aagctagagt aagtagttcg ccagttaata gtttgcgcaa cgttgttgcc attgctacag    5580
gcatcgtggt gtcacgctcg tcgtttggta tggcttcatt cagctccggt tcccaacgat    5640
caaggcgagt tacatgatcc cccatgttgt gcaaaaaagc ggttagctcc ttcggtcctc    5700
cgatcgttgt cagaagtaag ttggccgcag tgttatcact catggttatg gcagcactgc    5760
ataattctct tactgtcatg ccatccgtaa gatgcttttc tgtgactggt gagtactcaa    5820
ccaagtcatt ctgagaatag tgtatgcggc gaccgagttg ctcttgcccg gcgtcaatac    5880
gggataatac cgcgccacat agcagaactt taaaagtgct catcattgga aaacgttctt    5940
cggggcgaaa actctcaagg atcttaccgc tgttgagatc cagttcgatg taacccactc    6000
gtgcacccaa ctgatcttca gcatctttta ctttcaccag cgtttctggg tgagcaaaaa    6060
caggaaggca aaatgccgca aaaaagggaa taagggcgac acggaaatgt tgaatactca    6120
```

```
<210> SEQ ID NO 12
<211> LENGTH: 20
<212> TYPE: DNA
<213> ORGANISM: Artificial Sequence
<220> FEATURE:
<223> OTHER INFORMATION: T7 primer

<400> SEQUENCE: 12
taatacgact cactataggg                                                   20

<210> SEQ ID NO 13
<211> LENGTH: 20
<212> TYPE: DNA
<213> ORGANISM: Artificial Sequence
<220> FEATURE:
<223> OTHER INFORMATION: Forward primer of the rainbow trout EF-1 alpha
      gene

<400> SEQUENCE: 13
gatccagaag gaggtcacca                                                   20

<210> SEQ ID NO 14
<211> LENGTH: 20
<212> TYPE: DNA
<213> ORGANISM: Artificial Sequence
<220> FEATURE:
<223> OTHER INFORMATION: Reverse primer of the rainbow trout EF-1 alpha
      gene

<400> SEQUENCE: 14
ttacgttcga ccttccatcc                                                   20
```

-continued

```
<210> SEQ ID NO 15
<211> LENGTH: 24
<212> TYPE: DNA
<213> ORGANISM: Artificial Sequence
<220> FEATURE:
<223> OTHER INFORMATION: Forward primer of the rainbow trout BAFF-R gene

<400> SEQUENCE: 15
gacaaactgc tcatcacctg tatc                                          24

<210> SEQ ID NO 16
<211> LENGTH: 24
<212> TYPE: DNA
<213> ORGANISM: Artificial Sequence
<220> FEATURE:
<223> OTHER INFORMATION: Reverse primer of the rainbow trout BAFF-R gene

<400> SEQUENCE: 16
atatccagac agctggactc actg                                          24

<210> SEQ ID NO 17
<211> LENGTH: 23
<212> TYPE: DNA
<213> ORGANISM: Artificial Sequence
<220> FEATURE:
<223> OTHER INFORMATION: Forward primer of the 18S rRNA gene of
      Tetracapsuloides bryosalmonae

<400> SEQUENCE: 17
ggacactgca tgtgctgcat agt                                           23

<210> SEQ ID NO 18
<211> LENGTH: 23
<212> TYPE: DNA
<213> ORGANISM: Artificial Sequence
<220> FEATURE:
<223> OTHER INFORMATION: Reverse primer of the 18S rRNA gene of
      Tetracapsuloides bryosalmonae

<400> SEQUENCE: 18
ccatgctaga atgtccaggc act                                           23
```